US006444433B1

(12) United States Patent
Plhak et al.

(10) Patent No.: US 6,444,433 B1
(45) Date of Patent: Sep. 3, 2002

(54) DETECTION OF 2-METHYLISOBORNEOL BY MONOCLONAL ANTIBODY PRODUCTION

(75) Inventors: Leslie C. Plhak, Middleton, WI (US); Eun-Sung Park, Galveston, TX (US)

(73) Assignee: Board of Supervisors of Louisiana State University and Agriculture and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/490,547

(22) Filed: Jan. 24, 2000

(51) Int. Cl.$^7$ .............................................. G01N 33/543
(52) U.S. Cl. ...................... 435/7.92; 435/7.1; 436/547; 436/548; 530/388.1
(58) Field of Search ...................... 530/388.1; 436/547, 436/548, 815; 435/7.1, 7.94

(56) References Cited

FOREIGN PATENT DOCUMENTS

JP          08242883      *   9/1996

OTHER PUBLICATIONS

Ackermann et al., Biotechnology and Bioengineering, vol. 45, pp. 97–106, 1995.*
Harris et al., Biotechnology, vol. 11, pp. 1293–1297, 1993.*
Aoyama, "Studies on the earthy–musty odors in natural water (IV). Mechanism of earthy–musty odor production of actinomycetes," Journal of Applied Bacteriology, vol. 68, pp. 405–410 (1990).
Barrett, C.H., "Hybridomas and monoclonal antibodies," in Antibody Technique, eds. V.S. Malik and E.P. Lillehoj, Academic Press, pp. 71–102 (1994).
Chung et al., "Attempts to improve the sensitivity of an enzyme–linked immunosorbent assay for 2–methylisoborneol," Water Sci. Technol., vol. 25, pp. 89–95 (1992).
Chung et al., "Development of an enzyme–linked immunosorbent assay for geosmin," J. Agric. Food Chem., vol. 39, pp. 764–769 (1991).
Chung, S.-Y et al., "Development of an ELISA using polyclonal antibodies specific for 2–methylisoborneol," J. Agric. Food Chem., vol. 38, pp. 410–415 (1990).
Dionigi, C.P. et al., "Copper–containing aquatic herbicides increase geosmin biosynthesis by *Streptomyces tendae* and *Penicillium expansum*," Weed Science, vol. 43, pp. 196–200 (1995).
Goding, J.W., "Production of monoclonal antibodies," in Monoclonal Antibodies: Principle and Practice, Academic Press, pp. 59–103 (1986).
Harlow et al., "Monoclonal antibodies," in Antibodies: A Laboratory Manual, Cold Spring Harbor Laboratory, pp. 139–244 (1988).
Izaquirre, G. et al., "Geosmin and 2–methylisoborneol from cyanobacteria in three water supply systems," Applied and Environmental Microbiology, vol. 43, pp. 708–714 (1981).

Johnsen, P.B. et al., "Physiological approaches to the management of off–flavors in farm–raised channel catfish, *Ictalurus punctatus*," in Recent Developments in Catfish Aquaculture, pp. 141–161 (1994).
Krasner, S.W., "Analytical methods for the identification and quantification of earthy/musty flavors in drinking water: A review," Water Quality Bulletin, vol. 13, pp. 78–83 (1988).
Maga, J.A., "Musty/earthy aromas," Food Reviews International, vol. 3, pp. 269–284 (1987).
Martin, J.F. et al., Pharmacokinetics and tissue disposition of the off–flavor compound 2–methylisoborneol in the channel catfish (*Ictalurus punctatus*), Can. J. Fish. Aquat. Sci., vol. 47, pp. 544–547 (1990).
Martin, J.F. et al., "2–methylisoborneol implicated as a cause of off–flavor in channel catfish, *Ictalurus punctatus* (Rafinesque), from commercial culture ponds in Mississippi," Aquaculture and Fisheries Management, vol. 19, pp. 151–157 (1988).
Martin, J.F. et al., "Musty odor in chronically off–flavored channel catfish: Isolation of 2–methyleneboranane and 2–methyl–2–bornene," J. Agric. Food Chem., vol. 36, pp. 1257–1260 (1988).
Middlebrooks, B.L. et al., "A method for the production of monoclonal antibodies against geosmin (trans–1, 10–dimethyl–trans–(9)–decalol)," Paper presented at the Annual Meeting of the American Society for Microbiology, Abstract No. Q–133, Atlanta, Georgia, 1987.
Park, E.S., "Development of Monoclonal Antibody and Enzyme–linked Immunosorbent Assay for Detection of Off–flavor Compound 2–Methylisoborneol," Ph.D. Dissertation, Louisiana state University and Agricultural and Mechanical College, Dec. 1999.
Park et al., "Development of monoclonal antibody and enzyme immunoassay for 2–methylisoborneol," Abstract of a Paper presented at $4^{th}$ International Conference on Toxic Cyanobacteria, Sep. 27–Oct. 1, 1998, Beaufort, North Carolina.

(List continued on next page.)

Primary Examiner—Bao-Thuy L. Nguyen
(74) Attorney, Agent, or Firm—Bonnie J. Davis; John H. Runnels

(57) ABSTRACT

We have produced a hybridoma cell line that produces monoclonal antibodies (MAb) that bind effectively to 2-methylisoborneol (MIB). The MAbs were produced using a structurally related molecule, borneol, whose structure was minimally changed when complexed to the protein carrier. These MAbs detected MIB at approximately 0.01 to 1 ppb (or lower) when used in ELISA assays. Because these antibodies were produced as MAbs, their affinity characteristics remained constant. With access to MAb's, MIB can be easily detected at low levels using immunological techniques that are adapted to fast and easy field assays of large samples. For example, catfish could easily be assayed in the field for the presence of MIB prior to marketing.

11 Claims, 1 Drawing Sheet

OTHER PUBLICATIONS

Persson, P.–E., "Sensory properties and analysis of two muddy odor compounds, geosmin and 2–methylisoborneol, in water and fish," Water Research, vol. 14, pp. 1113–1118 (1980).

Peterson, H.G. et al, Physiological toxicity, cell membrane damage, and the release of dissolved organic carbon and geosmin by *Aphanizomenon flos–aquae* after exposure to water treatment chemicals, Wat. Res. vol. 29, pp. 1515–1523 (1995).

Tucker, C.S. et al., "Environment–related off–flavors in fish," in Aquaculture and Water Quality, D.E. Brune and J.R. Tomasso, eds., pp. 133–179 (1991).

Velzeboer, R. et al.,"Release of geosmin by *Anabaena circinalis* following treatment with aluminum sulphate," Wat. Sci. Tech., vol. 31, pp. 187–194 (1995).

Wood, S.F. et al., "2–Methylisoborneol, improved synthesis and a quantitative gas chromatographic method for trace concentrations producing odor in water," J. Chromatography, vol. 132, pp. 405–420 (1977).

Yurkowski, M. et al.,"Identification, analysis, and removal of geosmin from muddy–flavored trout," J. Fish. Res. Board Can., vol. 31, pp. 1851–1858 (1974).

* cited by examiner

DETECTION OF 2-METHYLISOBORNEOL BY MONOCLONAL ANTIBODY PRODUCTION

The development of this invention was partially funded by the Government under a USDA/SRAC grant awarded by the Department of Agriculture. The Government has certain rights in this invention.

This invention pertains to a method to detect 2-methylisoborneol using monoclonal antibodies and to a hybridoma cell line that produces such monoclonal antibodies.

Metabolites synthesized by some cyanobacteria, actinomycetes, and fungi are responsible for the earthy/musty or "off-flavor" taste in potable water and certain fish. See S. W. Krasner, "Analytical methods for the identification and quantification of earthy/musty flavors in drinking water: A review," Water Quality Bulletin, vol. 13, pp. 78–83 (1988); and P. B. Johnsen et al., "Physiological approaches to the management of off-flavors in farm-raised channel catfish, Ictalurus punctatus," in Recent Developments in Catfish Aquaculture, pp. 141–161 (1994). Two metabolites, which are the primary compounds responsible for this "off-flavor," are geosmin (1α, 10β-dimethyl-9α-decalol) and 2-methylisoborneol (1-R-exo-1,2,7,7-tetramethyl-bicyclo-[2.2.1]-heptan-2-ol) ("MIB"). These two compounds cause problems for the potable water and aquaculture industries because of the low concentrations of the compounds required to produce the "off-flavor" taste and because of the ubiquitous nature of the organisms that produce these metabolites.

The problem with earthy/musty flavors constitutes a significant restriction to the growth of the catfish industry. C. S. Tucker et al., "Environment-related off-flavors in fish," in Aquaculture and Water Quality, D. E. Brune and J. R. Tomasso, eds., pp. 133–179 (1991). Catfish cultured in ponds in the southern United States that are deemed unacceptable because of a "musty" flavor can be as high as 80% at any one time. J. F. Martin et al., "Pharmacokinetics and tissue disposition of the off-flavor compound 2-methylisoborneol in the channel catfish (Ictalurus punctatus), Can. J. Fish. Aquat. Sci., vol. 47, pp. 544–547 (1990); J. F. Martin et al., "Musty odor in chronically off-flavored channel catfish: Isolation of 2-methyleneboranane and 2-methyl-2-bornene," J. Agric. Food Chem., vol. 36, pp. 1257–1260 (1988); and J. F. Martin et al., "2-methylisoborneol implicated as a cause of off-flavor in channel catfish, Ictalurus punctatus (Rafinesque), from commercial culture ponds in Mississippi," Aquaculture and Fisheries Management, vol. 19, pp. 151–157 (1988). When "musty" fish cannot be harvested and brought to the market, the fish are held and fed until deemed "on-flavor" by an experienced human taster employed by the processing plant. However, during this time the fish grow beyond their optimal market size. Fish greater than about an 11 oz fillet are considered undesirable to both the producers and processors because they are more expensive to keep, the fat content of the fillet increases, automatic filleting is more difficult, and fish survival rates decrease as holding times increase.

Additionally, the earthy/musty flavors have been identified as a problem with trout and in potable water. See, for example, M. Yurkowski et al., "Identification, analysis, and removal of geosmin from muddy-flavored trout," J. Fish. Res. Board Can., vol. 31, pp. 1851–1858 (1974); G. Izaquirre et al., "Geosmin and 2-methylisoborneol from cyanobacteria in three water supply systems," Applied and Environmental Microbiology, vol. 43, pp. 708–714 (1981); and Aoyama, "Studies on the earthy-musty odors in natural water (IV). Mechanism of earthy-musty odor production of actinomycetes," Journal of Applied Bacteriology, vol. 68, pp. 405–410 (1990).

Methylisoborneol ("MIB") is a small terpenoid compound synthesized by cyanobacteria and actinomycetes and is illustrated below. It is fat-soluble and not easily volatilized.

Structure of MIB

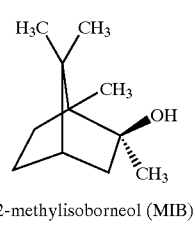

Structure of MIB 2-methylisoborneol (MIB)

MIB is believed to be taken up by fish through their gills and stored in fatty tissues. Fish with higher fat reserves are more prone to a "musty" flavor. Research related to quality control of catfish flavor has focused on the pond management by studying factors that influence the growth of algae or fungi populations, such as water quality, pH, oxygen levels, soil quality, fish density, feed quality and application rates, and water temperature. See, e.g., H. G. Peterson et al, Physiological toxicity, cell membrane damage, and the release of dissolved organic carbon and geosmin by Aphanizomenon flos-aquae after exposure to water treatment chemicals," Wat. Res. Vol. 29, pp. 1515–1523 (1995); C. P. Dionigi et al., "Copper-containing aquatic herbicides increase geosmin biosynthesis by Streptomyces tendae and Penicillium expansum," Weed Science, vol. 43, pp. 196–200 (1995); and R. Velzeboer et al., "Release of geosmin by Anabaena circinalis following treatment with aluminum sulphate," Wat. Sci. Tech., vol. 31, pp. 187–194 (1995). Although many approaches to eliminate algal growth have been tried, some algal growth is beneficial to maintain an adequate oxygen content in the water during daylight hours, especially when the temperature of the water is high. Because of this interaction between algae and oxygen and because of the large numbers of factors that affect both algal and fungal growth, controlling the "off-flavor" by pond management to control the algal density has proven difficult.

Another problem compounding the problem of "musty flavor" in aquaculture products is the difficulty in easily measuring the metabolites responsible. The "musty flavor" is caused by metabolites that are present at extremely low concentrations. The two methods used currently to detect both geosmin and MIB are human tasters and gas chromatography ("GC"). The human gustatory threshold of geosmin or MIB is approximately 10 to 30 ng/L in pure water. See, e.g., J. A. Maga, "Musty/earthy aromas," Food Reviews International, vol. 3, pp. 269–284 (1987); P. -E. Persson, "Sensory properties and analysis of two muddy odor compounds, geosmin and 2-methylisoborneol, in water and fish," Water Research, vol. 14, pp. 1113–1118 (1980); and S. F. Wood et al., "2-Methylisoborneol, improved synthesis and a quantitative gas chromatographic method for trace concentrations producing odor in water," J. Chromatography, vol. 132, pp. 405–420 (1977). Human sensory evaluation is the most sensitive method of detection currently available, but this method is subjective with a large degree of variation between tasters and even between tests by the same tester. Despite this problem, necessity has dictated the use of human flavor-tasters at catfish processing plants who have the authority to accept or reject catfish prior to harvest or delivery.

Gas chromatography ("GC") has been used to measure geosmin and MIB in analytical laboratories, but the use of this method by industry is limited. See, e.g., H. P. Dupuy et al., "Analysis for trace amounts of geosmin in water and fish," JAOCS, vol. 63, pp. 905–908 (1986). Analysis by GC requires that all hydrophilic species be completely removed from the sample. Thus, fish samples must be extracted and prepared using multi-step procedures that give low recovery rates and poor reproducibility. Recovery rates for known controls can be as low as 40 to 50%. More importantly, GC analysis requires skill and training, is costly, and is not adaptable to mass screening.

There is an unfilled need for a method to measure MIB that is more reliable and facile than either the sensory or gas chromatographic analyses currently available.

An immunoassay method to measure MIB has been tried. Polyclonal antibodies (PAb) were produced by binding compounds similar in structure to geosmin and MIB (argosmin and camphor, respectively) to a carrier protein to create a conjugate. The conjugate was then used to elicit an immune response and subsequent production of polyclonal antibodies. See S. -Y. Chung et al., "Development of an ELISA using polyclonal antibodies specific for 2-methylisoborneol," J. Agric. Food Chem., vol. 38, pp. 410–415 (1990); Chung et al., "Development of an enzyme-linked immunosorbent assay for geosmin," J. Agric. Food Chem., vol. 39, pp. 764–769 (1991); and Chung et al., "Attempts to improve the sensitivity of an enzyme-linked immunosorbent assay for 2-methylisoborneol," Water Sci. Technol., vol. 25, pp. 89–95 (1992). The polyclonal antibodies were unacceptable because of high non-specific binding and poor sensitivity (only detected down to 1 $\mu$g/ml), and because of the generation of false-positives from the presence of non-odiferous, structurally-related metabolites (e.g. argosmin, 2-methyleneborane and 2-methyl-2-borene). This poor sensitivity meant the PAbs were not useful to measure the low levels of MIB that causes "off-flavor" in foods. The detection limit using these PAbs was at least three orders of magnitude above the human sensory threshold and thus too high to be of practical use.

Monoclonal antibodies to geosmin analogs and geosmin derivatives bound to bovine serum albumin have been reported. See, B. L. Middlebrooks et al., "A method for the production of monoclonal antibodies against geosmin (trans-1,10-dimethyl-trans-(9)-decalol)," Abstract of a Paper presented at the Annual Meeting of the American Society for Microbiology, Abstract No. Q-133, Atlanta, Ga., 1987. There was no indication of the sensitivity of the MAbs.

Monoclonal antibodies have been reported to MIB, without disclosing the hybridoma cell-line. See Park et al., "Development of monoclonal antibody and enzyme immunoassay for 2-methylisoborneol," Abstract of a Paper presented at 4$^{th}$ International Conference on Toxic Cyanobacteria, Sep. 27–Oct. 1, 1998, Beaufort, N.C.

Areas in which a sensitive assay for MIB would be useful include measuring the quality or safety of potable water supplies, pond water, water filtering devices, aquacultural or fishery products (e.g., catfish, trout, shrimp, oysters, and clams), and agricultural products (e.g., hydroponic water supplies, and aquatic plants). Additionally, such an assay could monitor indoor air quality (e.g., fungal growth in air ducts), indicate a fungal infection in blood, and indicate fungal growth in grain storage containers.

We have produced a hybridoma cell line (F6b4G7b4, ATCC No. PTA-911) that produces monoclonal antibodies (MAb) that bind strongly to MIB. The MAbs were produced using a structurally related molecule, borneol, whose structure was minimally changed when complexed to the protein carrier. These MAbs detected MIB at approximately 0.01 to 0.1 ppb or lower when used in ELISA assays. Because these antibodies were produced as MAbs, their affinity characteristics will remain constant. Using these MAbs, MIB can be easily detected at low levels using immunological techniques that are adapted to fast and easy field assays to test a large number of samples.

Figure 1:
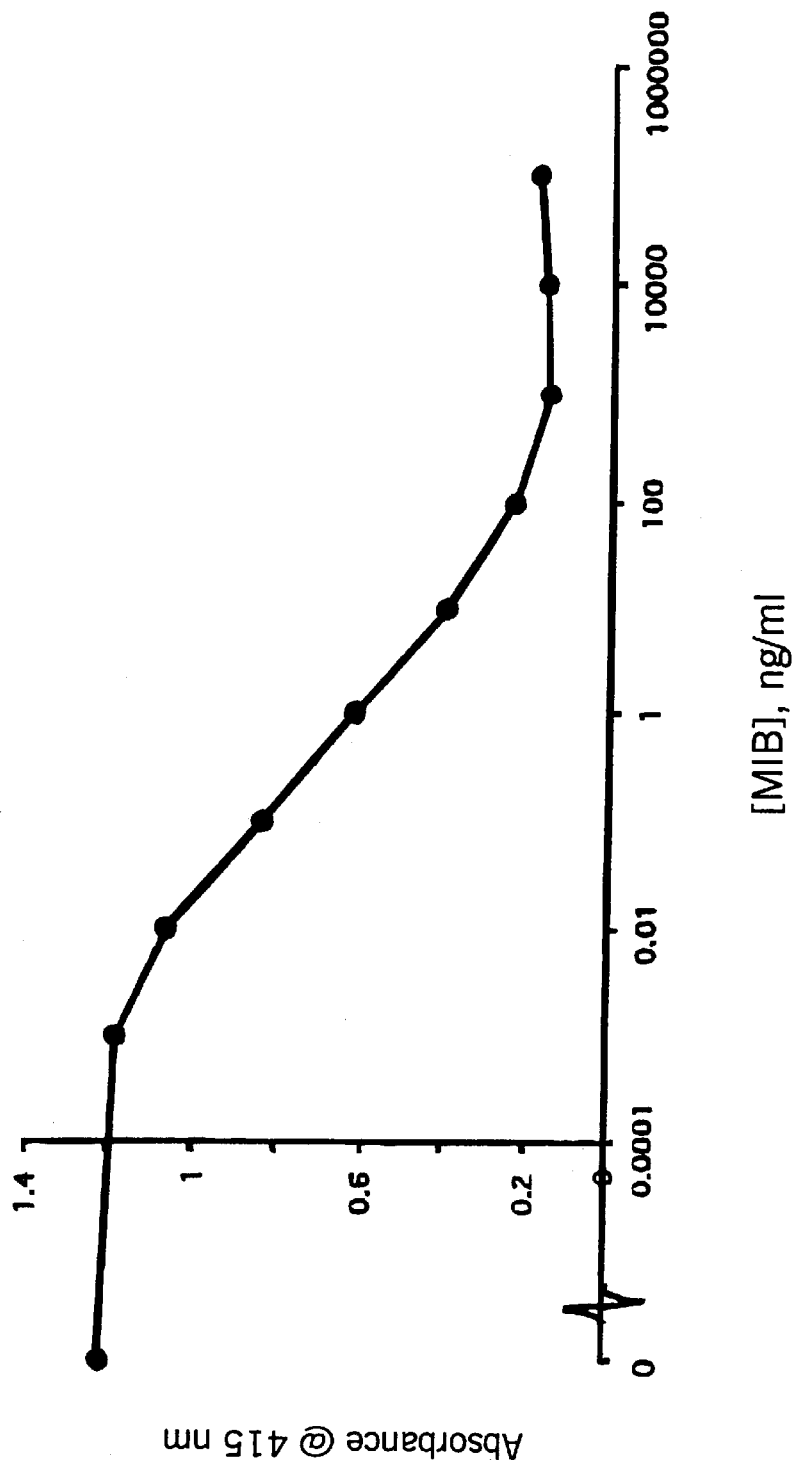
FIG. 1 illustrates a standard curve for a competitive ELISA for MIB using mouse serum PAb for borneol and MIB-BSA as a solid-phase conjugate.

We have created a hybridoma cell line (F6b4G7b4, ATCC No. PTA-911) that produces MAb's that strongly bind native MIB. MIB, as a small molecule, must be bound to a carrier molecule (e.g., *Limulus polyphemus* hemocyanin ("LPH")) to elicit an immune response and cause the production of antibodies. Often the binding of a molecule to the carrier protein causes a change in the structure of the small molecule, so that the antibodies produced are ineffective in binding the original unbound molecule. For the preparation of the LPH-bound immunogen, we used a small related molecule (borneol), rather than the actual compound of interest, MIB. This was done for several reasons: First, the lack of a methyl group in borneol allowed it to react faster and easier than MIB to the succinimide in an intermediate step. Second, borneol has a secondary hydroxyl group (not a teritary hydroxyl, as occurs in MIB), and thus would be less likely to dehydrate upon conjugation as may occur with MIB. Third, generating antibodies that recognize borneol-protein slightly more than MIB-protein or MIB, while retaining the ability to recognize these compounds, is advantageous during an indirect competitive immunoassay because it increases the sensitivity of the assay for free MIB. In a competitive assay, the free compound in the sample to be tested competes with a compound-protein adsorbed to a surface for the antibody binding sites. For example, in our competitive assay, the MIB free in the sample competes with a MIB-protein conjugate adsorbed to a surface for the antibody binding sites. The sensitivity of the assay depends on the strength of the antibody binding to the free analyte relative to the strength of the binding to the surface bound protein If the antibody had been made to MIB-LPH, the antibody would have a greater affinity for the MIB-protein than to free MIB which would require larger amounts of free MIB to compete effectively with MIB-protein for the antibody. By making the antibody to borneol-LPH, the affinity of the antibody for free MIB or for MIB-protein is more similar. Thus lower amounts of free MIB can successfully compete with the bound MIB-protein, and lower amounts of free MIB will be detected, improving the sensitivity of the assay.

Any cross-reactivity of the MAb produced with borneol would not present a problem in assaying for MIB under most situations. Borneol has not been reported to be synthesized by the same organisms as MIB; It is a component of essential oils from certain plants, e.g., thyme, sagebrush, persimmons, and mint.

Thus, in making the hybridoma cells to produce monoclonal anitbodies that would detect MIB, Borneol-LPH was used as the immunogen. Borneol-BSA, isoborneol-BSA, and MIB-BSA were compared to each other as solid-phase protein conjugates in the ELISA. The structures of borneol, isoborneol, and MIB are shown below.

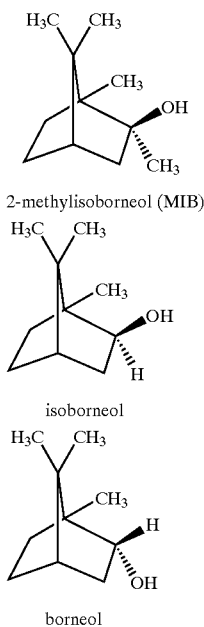

2-methylisoborneol (MIB)

isoborneol borneol

By starting with borneol, antibodies were produced that bound MIB with a greater affinity than that of the previous polyclonal antibodies produced by Chung et al., 1990. After immunizing mice using the borneol-LPH conjugate, a hybridoma cell line was produced using standard techniques. These MAbs were subsequently shown to bind MIB with great affinity, resulting in an assay sensitive to concentrations of MIB at the ng/ml range.

Mouse spleen cells from mice immunized several times with borneol-LPH were fused with myeloma cells, forming hybridoma cells. These were grown in vitro. After fusion, the parental myelomas were inhibited using selective medium. Hybridomas were screened for binding to MIB. Those selected were cloned to obtain stable monoclonal cell lines.

Once a reliable source of MAbs for MIB was generated, the MAb was used in an immunoassay to measure MIB. There are many types of immunoassays known in the art. The type chosen for any one assay depends in part on the label used to detect the Antibody-Antigen combination and include, for example, radioimmunoassay, enzyme-linked immunosorbent assay (ELISA), immunofluorescence assay, and luminoimmunoassay. Additionally, the assay may use a competitive, noncompetitive, or sandwich format. MIB was detected in the following examples using an antibody-capture, competitive, indirect ELISA. However, other immunoassay methods known in the art could easily be adapted to detect MIB using the novel MAb.

EXAMPLE 1

Source of Materials

Borneol and isoborneol were purchased from Aldrich Chemical Co. (Milwaukee, Wis.). Succinic anhydride, 4-(dimethylamino) pyridine, anisaldehyde, β-hydroxy-succinimide, 1,3,-dicyclohexylcarbodiimide, 2,2'-azino-bis (3-ethylbenz-thiazoline-6-sulfonic acid) ("ABTS"), ammonium carbonate, urea, bovine serum albumin ("BSA"), *Limulus polyphemus* hemocyanin ("LPH"), and sterile dimethyl sulfoxide were obtained from Sigma Chemical Co. (St. Louis, Mo.). Sterile polyethylene glycol (PEG 1500) in 75 $\mu$M HEPES buffer was purchased from Boehringer Mannheim (Indianapolis, Ind.).

The RIBI Adjuvant system for mice was purchased from Cedarlane Laboratories, Ltd. (Hornby, Ontario, Canada). Goat anti-mouse Ig G-horseradish peroxidase conjugate, purchased from Sigma Chemical Co. (St. Louis, Mo.), was used as a secondary antibody.

Phosphate-buffered saline ("PBS") solution was made as 0.9% sodium chloride in 0.01M phosphate buffer, pH 7.3. PBST was made by adding Tween 20 (0.05% by volume) to PBS before adjusting the pH.

Serum-free RPMI solution was Rosewell Park Memorial Institute ("RPMI") 1640, with the addition of L-glutamine (2 mM), sodium pyruvate (1 mM), penicillin (100 Units/ml), and streptomycin (100 $\mu$g/ml). All above chemicals were purchased from Sigma Chemical Co. (St. Louis, Mo.). Complete RPMI was serum-free RPMI with heat-inactivated fetal bovine serum ("FBS") (20% by volume). FBS was inactivated by heating to 56° C. for 30 min.

HT medium was Complete RPMI with 20% FBS, 100 $\mu$M sodium hypoxanthine, and 16 $\mu$M thymidine. HAT medium was HT medium with 0.4 $\mu$M aminopterin. Hypoxanthine, thymidine, and aminopterin were purchased as sterile 100× supplements from Gibco BRL (Gaithersburg, Md.).

EXAMPLE 2

Production of the Borneol Immunogen
Preparation of borneol-hemisuccinate.

First, 4-(dimethyl amino) pyridine (31.1 mg) was added to 9.1 ml pyridine, before adding succinic anhydride (487.7 mg). Borneol (168.4 mg) was added last, and the reaction mixture was heated under reflux with stirring for 53 hr at 65° C. The reaction was monitored by thin layer chromatography ("TLC"). The TLC assay used silica gel 60 F264 aluminum sheets (0.2 mm thick) from E. Merck (Darmstadt, Germany) with a mobile phase of 100 % ethyl acetate, 100% methanol, and 1% aqueous ammonia in a ratio of 80:20:1. The resulting bands were visualized by adding a mixture of 100% anisaldehyde, 100% acetic acid, and 100% sulfuric acid in a ratio of 0.5:50:1. The reaction was stopped with 20 ml $H_2O$. The resultant product was extracted three times, each time with 25 ml methylene chloride. The organic layer was collected from each extract, pooled, rotaevaporated to dryness, and then dried under vacuum in the presence of phosphorous pentoxide. The product produced was boreol-hemisuccinate.

Preparation of borneol-Limulus polyphemus hemocyanin ("LPH") Conjugate.

Borneol hemisuccinate, the entire amount produced as above, was dissolved in 4 mL anhydrous dimethylformamide ("DMF"). N,N'-Dicyclohexyl carbodiimide (87.9 mg) and N-hydroxy succinimide (107 mg) were added. The mixture was stirred 12 hr at 4° C. to form an active ester mixture. Half of the active ester reaction mixture (about 2 ml) was filtered through glass wool into a LPH/PBS solution (25.1 mg LPH dissolved in 4 ml PBS). This mixture was stirred for 22 hr at 4° C. and then dialyzed against three consecutive solutions: 2 hr against 8 M urea (0.9 L); 1 hr against 50 mM ammonium carbonate (2 L); and finally overnight against 25 mM ammonium carbonate (4 L). The final dialyzed product was lyophilized to 23.1 mg.

EXAMPLE 3

Immunization of Mice

Four-month BALB/c female mice (Louisiana State University breeding colony, Baton Rouge, La.) were maintained at 20° C., a 12-hr light cycle, and fed Rodent Chow 5001 (PMI Nutrition, Inc., St. Louis, Mo.). Prior to immunization, blood samples (200 µl) were obtained from two mice. The two mice were then immunized with 0.3 mg borneol-LPH conjugate in 0.6 ml sterile RIBI adjuvant in PBS. Two 0.1 ml injections were made in each mouse, one subcutaneously and the other intraperitoneally. Subsequent injection boosts were made in the same manner on days 21, 46, and 67 after the initial injections. Blood samples were collected 1 wk after the day of each immunization. Each blood sample was allowed to clot at 37° C. for 30 min and then stored at 4° C. overnight. The samples were then centrifuged at 12,000 rpm to separate the serum from the blood cells. The serum was assayed for the presence of antibodies to MIB.

EXAMPLE 4

Enzyme-Linked Immunosorbent Assay (ELISA)

Preparation of Solid-Phase Protein Conjugates

To measure the presence of a small molecule like MIB, a competitive indirect ELISA was used. In this method, a finite amount of an immobilized compound (the solid-phase conjugate) competes with the small molecule to be detected for a finite number of antibody-binding sites. By measuring the antibody partitioning between the immobilized and soluble phases, the amount of soluble compound can be determined. The solid-phase conjugate used in most ELISA assays was MIB-bovine serum albumin conjugate. To make this conjugate, MIB hemisuccinate was prepared and then reacted with bovine serum albumin ("BSA"). To prepare MIB hemisuccinate, first 4-(Dimethylamino) pyridine (38.4 mg) was added to 8.9 ml pyridine. Into this mixture, succinic anhydride (445.7 mg) was dissolved, and then MIB (82 mg) was added. The mixture was heated under reflux for 3 days at 74° C. and monitored with TLC as described above in Example 2. The reaction was stopped by adding 25 ml $H_2O$ and extracted three times, each time with 25 ml methylene chloride. The methylene chloride extracts were combined, roto-evaporated, redissolved in 25 ml $H_2O$, and then extracted again with methylene chloride twice, with 45 ml and 25 ml, respectively. The extracts were combined, roto-evaporated, and dried under vacuum in the presence of phosphorous pentoxide. The weight of the final MIB hemisuccinate product was 154 mg.

The MIB hemisuccinate product (154 mg) was dissolved in 5 ml anhydrous dimethylformamide; and then N-hydroxysuccinimide (87 mg) and N,N'-dicyclohexylcarbodiimide (117 mg) were added. This reaction mixture was stirred 24 h at 4° C. to form the active ester of MIB hemisuccinate. The active ester reaction mixture (about 2 ml) was filtered through glass wool into a BSA solution of 127.3 mg BSA dissolved in 3 ml PBS. This mixture was stirred for 2 days at 4° C., and then dialyzed against three successive solutions: 2 hr against 8 M urea (0.9 L); 4 hr against 50 mM ammonium carbonate (2 L); and finally 5 hr against 25 mM ammonium carbonate (4 L). The dialyzed sample was lyophilized to obtain the resultant product, which weighed 102.5 mg. To obtain only soluble conjugate, some of the dialysis product (80.2 mg) was dissolved in 15 ml 50 mM ammonium carbonate, and centrifuged until the supernatant was clear. The supernatant was lyophilized again. The weight of the final purified MIB-BSA conjugate was 27.6 mg.

In a similar way, isoborneol-BSA and borneol-BSA were produced by first making isoborneol hemisuccinate and borneol hemisuccinate, respectively, and then complexing each with BSA as described above.

Screening sera for antibody titer.

Antibody titer from the immunized mouse serum was tested using a checkerboard enzyme immunoassay. A stock solution (100 µg/ml) of the solid-phase MIB-BSA conjugate was prepared in PBS. This solution was serially diluted three times with PBS to obtain four different concentrations: 100 µg/ml, 10 µg/ml, 1 µg/ml, and 0.1 µg/ml. Each row of a microtiter plate was filled with 100 µl of one of the above concentrations. The plates were then stored overnight at 4° C. The next day, the solutions were removed from the plate with a sharp shake of wrist, and each well blocked with 200 µl of 1% gelatin in PBS for 30 min at 37° C. The wells were then washed three times with 200 µl PBST for 5 min at room temperature.

Five different dilutions of mouse serum (1/500; 1/1,000; 1/5,000; 1/10,000; and 1/100,000) were prepared by adding the appropriate amount of 1% BSA in PBS. Fifty (50) µl $H_2O$ was added to each well of the microtiter plate. Immediately, 50 µl diluted serum was added in a pattern such that each column of the microtiter plate represented a different serum concentration. After incubating for 30 min at 37° C., the wells were emptied and washed three times as before with 200 µl PBST. Goat anti-mouse IgG-horseradish peroxidase conjugate was diluted 1/1,000; and 100 µl of the diluted solution was added to each well. The plates were again incubated for 30 min at 37° C. and washed as before. A solution (100 µl) of peroxidase substrate (2,2'-Azino-bis (3-Ethylbenz-thiazoline-6-sulfonic acid) ("ABTS," 0.5 mg/ml) with 0.01% hydrogen peroxide in 0.1 M citrate buffer (pH 3.8)) was added to each well. After 30 min at room temperature, absorbance at 405 nm was measured.

To test the ability of the antibody to bind free MIB, an indirect competitive ELISA was performed. Microplates were coated with MIB-BSA conjugate (1 µg/ml) in PBS. Incubations were performed as described above, but serum was used at 1/5000 dilution and the 50 µl of $H_2O$ was replaced with 50 µl 5% methanol-containing MIB. The MIB-methanol solution had been serially diluted to generate different concentrations as described above for mouse serum.

One week after the second injection (53 days after initial immunization), antibody ("Ab") could be detected in the mouse serum. Using ELISA, Ab from serum was shown to bind to solid-phase MIB conjugate and to be competitively removed using free MIB.

Competitive enzyme immunoassay.

For competitive assays, inhibition curves were constructed using 10 pg/ml to 100 µg/ml MIB in 10% methanol. Optimum concentrations of antibody and solid-phase protein conjugate were predetermined by checkerboard ELISA as described above for the screening of mouse serum, except that different incubation times and temperatures were used. Microplates were coated with different concentrations of solid-phase protein conjugate (either borneol-BSA, isoborneol-BSA, or MIB-BSA) (200 µl/well) and stored overnight at 4° C. Blocking and washing steps were as described above for mouse serum testing. Pre-diluted anti-borneol MAb (100 µl) was used as a primary antibody and serially diluted MIB solution (from 10 pg/ml to 100 µg/ml) in 10% methanol was added for the competition. After incubating for 2 hr at room temperature, the wells were washed three times with 200 µl PBST. Pre-diluted goat anti-mouse IgG-peroxidase conjugate (1/2000) was added to the wells for use as a secondary antibody, and the wells further incubated at room temperature for 2 hr. The wells were then washed as before. A solution (100 µl) of peroxidase substrate (2,2'-azino-bis-3-ethylbenz-thiazoline-6-sulfonic acid (ABTS, 0.5 mg/ml) with 0.01% hydrogen peroxide in 0.1 M citrate buffer (pH 3.8)) was added to each well. After incubating for 30 min at room temperature, the absorbance at 405 nm was measured using a SPECTRA-MAX®. microplate spectrophotometer (Molecular Devices Corp., Sunnyvale, Calif.). The results, expressed as A/Ao, were calculated as described in D. M. Rocke et al., "Statistical design of ELISA protocols," J. Immunol. Methods, vol. 132, pp. 247–254 (1990). The formula used is as follows:

$$A/Ao=(A_{405\ nm}\ \text{sample})/(A_{405\ nm}\ \text{blank})$$

A graphs was constructed with A/Ao as the y-axis and MIB concentration as the x-axis, as seen in FIG. 1. Four parameter curves were determined using the data generated from standard solutions using SOFTMAX®, Pro Version 2.6 (Molecular Devices Corp., Sunnyvale, Calif.).

EXAMPLE 5

Production of a Cell Line to Produce Monoclonal Antibodies

Cell Fusion and Selection

Mouse myeloma cells (NS-1, ATCC# TIB 18) were grown in sterile tissue culture flasks using complete RPMI with 20% fetal bovine serum at general incubation conditions (37° C., 5% $CO_2$, and 90–100% humidity). Cells were subcultured every 2 to 4 days using dilutions in the range of $\frac{1}{10}$ to $\frac{1}{20}$ to maintain cell density from about: $10^5$ to $10^6$ cells/ml. Viable cells were counted as a $\frac{1}{10}$ or $\frac{1}{5}$ dilution of cells suspended in 0.25% (w/v) trypan blue in PBS. On the day of fusion, actively dividing myeloma cells were centrifuged at 250 g for 10 min. The cells were then combined with 15 ml serum-free RPMI media and washed twice with serum-free RPMI media. After the final washing, the cells were resuspended in 15 ml serum-free RPMI media; and the viable cells counted.

Three days after the final injection (i.e., 70 days after the initial immunization), the mouse with the higher Ab titer was asphyxiated using $CO_2$; and the spleen was removed under sterile conditions. The spleen was washed with 10 ml serum-free RPMI media and placed in a petri dish containing 10 ml serum-free RPMI media. Splenocytes were gently teased and flushed from the spleen using two sterile needles (21 gauge) and syringes. The splenocytes were transferred to a 15 ml conical centrifuge tube and centrifuged at 250 g for 5 min. The cells were washed twice with 10 ml serum-free RPMI. After the last centrifugation, any remaining red blood cells were lysed by suspending the cells in 4 ml 0.8% $NH_4Cl$ for 1.5 min. The remaining intact cells (splenocytes) were centrifuged at 250 g for 10 min, resuspended in 10 ml serum-free RPMI, counted, and immediately used for fusion.

Splenocytes ($1.2\times10^7$) and myeloma cells ($8.7\times10^5$) were combined in a ratio of 13:1. The combined cells were gently mixed and centrifuged at 800 g for 5 min. One (1) ml 1% polyethylene glycol ("PEG") 1500 in HEPES buffer was added to the cells with gentle mixing and stirring for 2 min at room temperature. Serum-free RPMI (1 ml) was slowly added over the next two minutes, with an additional 9 ml added over the next 3 min. The cell suspension was then centrifuged in 8 ml HAT medium and plated out by adding 100 µl cell suspension to each well of a 96-well sterile plate. Control myeloma cells were added to 8 wells. The cells were cultured in HAT medium for the first 10 days. For the next 10 days, cells were subcultured in HT medium. After 5 days, supernatant from each well was screened for antibodies by incubating a 20 µl aliquot on microtiter plates that had been previously coated with 10 µg/ml MIB-BSA conjugate, blocked, and washed as described above in Example 4. The relative antibody (Ab) activity was expressed as the absorbance ($A_{405\ nm}$) measured after a 30 min peroxidase reaction at room temperature. Cells from three wells that showed relative Ab activities greater than 1.0 were subcultured in complete RPMI with 20% serum in 24-well plates. After subculturing, one of the original wells stopped producing Ab, so only the cells from two of the original positive wells were actually cloned.

The fusion of splenocytes with myeloma cells gave rise to between 5 and 10 hybridomas per well, for a total of approximately 400 hybridoma cells. These hybridoma cells actively grew in the presence of aminopterin in HAT medium, while control myeloma cells did not. Five days after fusion, ELISA screening of supernatant revealed three wells that were producing antibody specific for MIB.

Cell cloning.

Cells from wells producing antibody specific for MIB were cloned by limiting dilution as described by the following references: C. H. Barrett, "Hybridomas and monoclonal antibodies," in Antibody Technique, eds. V. S. Malik and E. P. Lillehoj, Academic Press, pp. 71–102 (1994); J. W. Coding, "Production of monoclonal antibodies," in Monoclonal Antibodies: Principle and Practice, Academic Press, pp. 59–103 (1986); and Harlow et al., "Monoclonal antibodies," in Antibodies: A Laboratory Manual, Cold Spring Harbor Laboratory, pp. 139–244 (1988). Conditioned medium was prepared by growing myeloma cells in complete RPMI containing 20% fetal bovine serum for 3 days, centrifuging the cell suspension at 250 g for 10 min, and passing the supernatant through a 0.2 µm filter. This filtered medium was refortified with 20% fetal bovine serum and 1% 200 µM glutamine. Cells were plated at concentrations of 10, 1 and 0.1 cells per 200 µl of conditioned medium in 96-well plates (30 wells of each concentration). Macroscopic colonies became visible 1 to 2 wk after cloning commenced. Clones were assayed after 10 days for Ab production. Positive clones were transferred to 24-well plates to test cell viability and activity. The cloning procedure was repeated three times to ensure stability of cell lines.

Cells were cloned from wells positive for Ab production, the specificity of the produced Ab in a competitive assay, and cell growth. Five different cell lines were cloned. The cell line that was designated "F6b4G7b4" (ATCC No. PTA-911) was cloned three times and found to be the most vigorous grower that produced relatively high titres of MAb. Supernatants from 200 ml of F6b4G7b4 cell suspensions cultured in RPMI media with 20% fetal bovine serum were collected by first centrifuging at 200 g for 5 min. MAb was purified from the supernatants by ammonium sulfate precipitation and dialysis as described above. Optimal dilution of MAb and concentration of solid-phase protein conjugate were decided using a checkerboard ELISA.

Standard binding curves were constructed using MIB solutions (1 pg/ml to 100 µg/ml) in 10% MeOH and pre-diluted MAb of F6b4G7b4 (a 1:125 dilution), with a solid-phase protein conjugate (MIB-BSA, 0.5 µg/ml) in indirect competitive ELISA. FIG. 1 illustrates such a standard curve and demonstrates that the MAb can detect MIB down to pg/ml (parts per trillion) levels.

A sample of the cloned hybridoma cell line F6b4G7b4 was deposited with the American Type Culture Collection (ATCC), 10801 University Boulevard, Manassas, Va. 20110-2209, on Nov. 3, 1999, and was assigned ATCC Accession No. PTA-911. This deposit was made pursuant to a contract between ATCC and the assignee of this patent application, Board of Supervisors of Louisiana State University and Agricultural and Mechanical College. The contract with ATCC provides for permanent and unrestricted availability of the cell line to the public on the issuance of the U.S. patent describing and identifying the deposit or the publication or the laying open to the public of any U.S. or foreign patent application, whichever comes first, and for the availability of the progeny of the cell line to one determined by the U.S. Commissioner of Patents and Trademarks to be entitled thereto under pertinent statutes and regulations. The assignee of the present application has agreed that if the cell line on deposit should die or be lost or destroyed when cultivated under suitable conditions, it will be promptly replaced on notification with a viable culture of the same cell line.

EXAMPLE 6

In a competitve ELISA, the detection sensitivity for the free analyte can be increased by decreasing the affinity of the MAb for the solid-phase protein conjugate. For example, the affinity of the MAb for protein-bound borneol-hemisuccinate may be higher than its affinity for free MIB, which negatively affects the sensitivity of the indirect competitive ELISA. The sensitivity (i.e., the detection range) in an indirect competitive ELISA depends on how effectively free MIB binds to MAb in competition with the bound solid-phase protein conjugate. The sensitivity could be improved by changing the solid-phase conjugate so that the MAb would still bind to the solid-phase conjugate, but would bind more effectively to MIB.

Because borneol-LPH was used as the initial immunogen, two new solid-phase conjugates, isoborneol-BSA and MIB-BSA, were made as described in Example 4. Isoborneol is an isomer of borneol with a different orientation of the hydroxyl group. MIB is an analog of borneol with an additional methyl group.

Table 1 demonstrates the effect of the three solid-phase conjugate types (MIB-BSA, borneol-BSA, and isoborneol-BSA) on the sensitivity of the ELISA. Because the antibody was made using borneol-LPH as an immunogen, the MAb showed a higher affinity for borneol-LPH than either isoborneol or MIB. This is demonstrated by the poorer assay sensitivity (higher $I_{50}$ values) when borneol-BSA was used as a solid-phase conjugate in the ELISA. During this version of the assay, free MIB competed with the borneol-BSA solid-phase conjugate for the binding of MAb. The extra methyl group on MIB decreased affinity of MAb to MIB compared to its affinity for the borneol-BSA. By substituting the MIB-BSA as the solid-phase conjugate, the affinity of MAb for the free MIB, relative to the affinity for the solid-phase conjugate, was optimum. Thus the sensitivity of the ELISA for measuring MIB was optimum when the MIB-BSA conjugate was used for the solid phase. Using the MIB-BSA conjugate at a concentration of 0.5 µg/ml with a low concentration of MAb (1/250 dilution of the cell culture supernatant), the detection limit of the assay for free MIB (defined as the concentration of MIB giving $A/A_o$ values of 0.8) was less than 10 pg/ml (less than 10 parts per trillion).

TABLE 1

Sensitivity of the ELISA Using Three Solid-Phase Conjugates

| Ab dilution | Solid phase conjugate concentration (µg/ml) | $I_{50}$ values (ng/ml) | | |
|---|---|---|---|---|
| | | MIB-BSA | isoborneol-BSA | borneol-BSA |
| 1/250 | 0.50 | 0.284 | 1 | 16 |
| 1/125 | 1 | 0.041 | 1 | 22 |
| 1/250 | 1 | 4 | 12 | 42 |

Using the MAb generated by the new cell line, other immunoassays can be developed to measure the amount of MIB, including, for example, radioimmunoassay, immunofluorescence assay, and luminoimmunoassay. Additionally, field kits may easily be produced by methods known commercially to enable the detection of MIB in an easy, inexpensive manner that can handle a large number of samples. Areas in which such assays would be useful include measuring the quality or safety of potable water supplies, pond water, water filtering devices, aquacultural or fishery products (e.g., catfish, trout, shrimp, oysters, and clams), and agricultural products (e.g., hydroponic water supplies, and aquatic plants). Additionally, such an assay could monitor indoor air quality (e.g., fungal growth in air ducts), blood to indicate an infection, and fungal growth in grain storage containers.

The complete disclosures of all references cited in this specification are hereby incorporated by reference. Also incorporated by reference is the complete dislosure of the following dissertation: E. S. Park, "Development of Monoclonal Antibody and Enzyme-linked Immunosorbent Assay for Detection of Off-flavor Compound 2-Methylisoborneol," Ph.D. Dissertation, Louisiana state University and Agricultural and Mechanical College, December 1999. In the event of an otherwise irreconcilable conflict, however, the present specification shall control.

We claim:

1. A hybridoma cell line having ATCC accession number PTA-911, wherein said cell line monoclonal antibodies against 2-methylisoborneol.

2. A hybridoma cell line as in claim 1, wherein said cell line is the cell line with ATCC accession number PTA-911.

3. A monoclonal antibody produced by the hybridoma cell line of claim 1.

4. A method to assay a sample for the presence of 2-methylisoborneol, comprising the steps of:
   (a) combining the sample with a monoclonal antibody produced by the hybridoma cell line of claim 1;
   (b) incubating the sample with the antibody for a time and under conditions sufficient for the formation of antibody-antigen complexes; and
   (c) detecting the presence of antibody-antigen complexes formed in step (b) as an indication of the presence of 2-methylisoborneol.

5. A method as in claim 4, wherein the sample is selected from the group consisting of catfish, clam, oyster, trout, shrimp, potable water, pond water, air duct, air trap, air filter, blood, and grain storage containers.

6. A method as in claim 4, wherein the sample comprises catfish or a catfish fillet.

7. A method as in claim 4, wherein the assay is selected from the group consisting of radioimmunoassay, enzyme-linked immunosorbentassay, immunofluorescence assay, and luminoimmunoassay.

8. A method as in claim 4, wherein the assay comprises an enzyme-linked immunosorbent assay.

9. A method as in claim 4, wherein the assay comprises a competitive immunoassay.

10. A method as in claim 4, wherein the assay comprises a quantitative assay.

11. A method as in claim 4, wherein the assay comprises a qualitative assay.

* * * * *